US006849599B2

(12) United States Patent
Calabresi et al.

(10) Patent No.: US 6,849,599 B2
(45) Date of Patent: Feb. 1, 2005

(54) COMBINATION DRUG THERAPY

(75) Inventors: Paul Calabresi, Barrington, RI (US); James Darnowski, Barrington, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 09/802,094

(22) Filed: Mar. 8, 2001

(65) Prior Publication Data

US 2002/0107191 A1 Aug. 8, 2002

Related U.S. Application Data

(60) Provisional application No. 60/187,852, filed on Mar. 8, 2000.

(51) Int. Cl.$^7$ .................. A61K 38/00; A61K 38/43; A61K 38/51; C12N 9/90; C07K 17/00
(52) U.S. Cl. .................. 514/12; 424/94.1; 424/94.5; 435/233; 530/399
(58) Field of Search .................. 424/94.1, 94.5; 514/2; 435/233; 530/399

(56) References Cited

U.S. PATENT DOCUMENTS

| | | | |
|---|---|---|---|
| 5,192,744 A | 3/1993 | Bouck et al. .................. 514/8 |
| 5,670,507 A | 9/1997 | Rice et al. .................. 514/263 |
| 5,786,344 A | 7/1998 | Ratain et al. .................. 514/100 |
| 5,840,692 A | 11/1998 | Deutch et al. .................. 514/12 |
| 5,843,994 A | 12/1998 | Samid .................. 514/510 |
| 5,886,026 A | 3/1999 | Hunter et al. .................. 514/449 |
| 5,981,568 A | 11/1999 | Kunz et al. .................. 514/411 |
| 5,994,309 A | 11/1999 | Mazar et al. .................. 514/16 |
| 5,994,341 A | 11/1999 | Hunter et al. .................. 514/210 |
| 6,100,273 A | 8/2000 | Besterman et al. ......... 514/279 |
| 6,406,693 B1 * | 6/2002 | Thorpe et al. |

FOREIGN PATENT DOCUMENTS

| | | |
|---|---|---|
| WO | WO 91/10424 | 7/1991 |
| WO | WO 92/14470 | 9/1992 |
| WO | WO 93/09782 | 5/1993 |
| WO | WO 9601127 A1 | 1/1996 |
| WO | WO 9843618 A2 | 10/1998 |
| WO | WO 9910523 A1 | 3/1999 |
| WO | WO 9910524 A1 | 3/1999 |
| WO | WO 9910525 A1 | 3/1999 |
| WO | WO 9954445 A2 | 10/1999 |

OTHER PUBLICATIONS

O'Leary et al. (Clinical Cancer Res. Jan. 1999; 5:181–187).*
Sheibani et al. (Biochem Biophys Res commun Jan. 7, 2000; 267(1):257–61,).*
Streit et al. (Proc Natl Acad Sci USA Dec. 21, 1999; 96(26):14888–93).*
Biosciences Information Service. (2000). Database Accession No. PREV200000275647 (XP002180182).
International Search Report. PCT/ US 01/ 07472. Issued on Dec. 13, 2001.
Clements et al., "Antiangiogenic potential of camptothecin and topotecan," Cancer Chemotherapy and Pharmacology, V44, N1, p. 39–48.
Clements et al., "Inhibition of Angiogenesis and Proliferation of Normal Endothelial Cells by Camptothecin," 1998, FASEB J., N5, 2, S(Mar. 20), p. 5499.
Clements et al., "Camptothecin exhibits selective cytotocicity towards human breast carcinoma as compared to normal bovine endothelial cells in vitro," 1996, Anticancer Drugs 7:851.
Guo et al., "Thrombospondin 1 and Type I Repeat Peptides of Thrombospondin 1 Specifically Induce Apoptosis of Endothelial Cells," Cancer Res. 57/9 (1735–1742).
Hsiang et al., "DNA Topoisomerase I–mediated DNA Cleavage and Cytotoxicity of Camptothecin Analogues," 1989, Cancer Research, 49:4385–4389.
Jaxel et al., "Structure–Activity Study of the Actions of Camptothecin Derivatives on Mammalian Topoisomersae I: Evidence for a Specific Receptor Site and a Relation to Antitumor Activity," Cancer Research. 49:1465–1469.
Kakeji et al., "Preclinical studies of the combination of angiogenic inhibitors with cytotoxic agents," Investigational New Drugs, 7(1):39–48.
Kantarjian et al., "New Developments in the Treatment of Acute Myeloid Leukemia: Focus on Topotecan," Seminars in Hemotology, 36/4 Suppl. 8 (16–5).
O'Leary et al., "Antiangiogenic Effects of Camptothecin Analogues 9–Amino–20(S)–camptothecin, Topotecan, and CPT–11 Studies in the Mouse," 1999, Clinical Cancer Research, 5:181–7.
Polverini et al., "Assay and Purification of Naturally Occuring Inhibitor of Angiogenesis," 1991, Methods. Enzymol. 198:440–450.

* cited by examiner

*Primary Examiner*—Gary Nickol
*Assistant Examiner*—Christopher Yaen
(74) *Attorney, Agent, or Firm*—Mintz, Levin, Cohn, Ferris, Glovsky and Popeo, P.C.; Ingrid A. Beattie

(57) ABSTRACT

The invention provides antineoplastic composition containing an inhibitor of angiogenesis and an inhibitor of DNA topoisomerase type I enzyme activity.

7 Claims, No Drawings

SEQUENCE LISTING

```
<160> NUMBER OF SEQ ID NOS: 6

<210> SEQ ID NO 1
<211> LENGTH: 57
<212> TYPE: PRT
<213> ORGANISM: Artificial Sequence
<220> FEATURE:
<223> OTHER INFORMATION: Thrombospondin-1/2 fragment
<221> NAME/KEY: VARIANT
<222> LOCATION: (1)..(3)
<223> OTHER INFORMATION: Wherein X is any amino acid.
<221> NAME/KEY: VARIANT
<222> LOCATION: (5)..(6)
<223> OTHER INFORMATION: Wherein X is any amino acid.
<221> NAME/KEY: VARIANT
<222> LOCATION: (8)..(9)
<223> OTHER INFORMATION: Wherein X is any amino acid.
<221> NAME/KEY: VARIANT
<222> LOCATION: (11)..(12)
<223> OTHER INFORMATION: Wherein X is any amino acid.
<221> NAME/KEY: VARIANT
<222> LOCATION: (14)..(27)
<223> OTHER INFORMATION: Wherein X is any amino acid.
<221> NAME/KEY: VARIANT
<222> LOCATION: (29)..(51)
<223> OTHER INFORMATION: Wherein X is any amino acid.
<221> NAME/KEY: VARIANT
<222> LOCATION: (53)..(56)
<223> OTHER INFORMATION: Wherein X is any amino acid.

<400> SEQUENCE: 1

Xaa Xaa Xaa Trp Xaa Xaa Trp Xaa Xaa Trp Xaa Xaa Cys Xaa Xaa Xaa
 1               5                  10                  15

Xaa Xaa Xaa Xaa Xaa Xaa Xaa Xaa Xaa Xaa Xaa Cys Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Cys Xaa Xaa Xaa Xaa Cys
    50                  55

<210> SEQ ID NO 2
<211> LENGTH: 4
<212> TYPE: PRT
<213> ORGANISM: Artificial Sequence
<220> FEATURE:
<223> OTHER INFORMATION: Thrombospondin 1/2 fragment

<400> SEQUENCE: 2

Trp Ser Pro Ser
 1

<210> SEQ ID NO 3
<211> LENGTH: 4
<212> TYPE: PRT
<213> ORGANISM: Artificial Sequence
<220> FEATURE:
<223> OTHER INFORMATION: Thrombospondin 1/2 fragment

<400> SEQUENCE: 3

Lys Arg Phe Lys
 1

<210> SEQ ID NO 4
<211> LENGTH: 6
<212> TYPE: PRT
```

```
-continued

<213> ORGANISM: Artificial Sequence
<220> FEATURE:
<223> OTHER INFORMATION: Thrombospondin 1/2 fragment

<400> SEQUENCE: 4

Cys Ser Val Thr Cys Gly
 1               5

<210> SEQ ID NO 5
<211> LENGTH: 57
<212> TYPE: PRT
<213> ORGANISM: Artificial Sequence
<220> FEATURE:
<223> OTHER INFORMATION: Thrombospondin 1 fragment

<400> SEQUENCE: 5

Asp Gly Gly Trp Ser His Trp Ser Pro Trp Ser Ser Cys Ser Val Thr
 1               5                  10                  15

Cys Gly Asp Gly Val Ile Thr Arg Ile Arg Leu Cys Asn Ser Pro Ser
            20                  25                  30

Pro Gln Met Asn Gly Lys Pro Cys Glu Gly Glu Ala Arg Glu Thr Lys
        35                  40                  45

Ala Cys Lys Lys Asp Ala Cys Pro Ile
    50                  55

<210> SEQ ID NO 6
<211> LENGTH: 57
<212> TYPE: PRT
<213> ORGANISM: Artificial Sequence
<220> FEATURE:
<223> OTHER INFORMATION: Thrombospondin 2 fragment

<400> SEQUENCE: 6

Asp Gly Gly Trp Ser His Trp Ser Pro Trp Ser Ser Cys Ser Val Thr
 1               5                  10                  15

Cys Gly Val Gly Asn Ile Thr Arg Ile Arg Leu Cys Asn Ser Pro Val
            20                  25                  30

Pro Gln Met Gly Gly Lys Asn Cys Lys Gly Ser Gly Arg Glu Thr Lys
        35                  40                  45

Ala Cys Gln Gly Ala Pro Cys Pro Ile
    50                  55
```

COMBINATION DRUG THERAPY

RELATED APPLICATION

This application claims the benefit from provisional application Ser. No. 60/187,852, filed on Mar. 8, 2000, the contents of which is hereby incorporated by reference96/0.

BACKGROUND OF THE INVENTION

This invention relates to cancer chemotherapy.

Chemotherapy for cancer is used primarily for the treatment of nonoperable or metastatic tumors or to supplement primary surgical therapy. Traditional chemotherapeutic approaches to cancer treatment involve administering agents which are cytotoxic to tumor cells. However, often such agents also affect normal cells resulting in adverse side effects.

SUMMARY OF THE INVENTION

The invention features a combination of therapeutic agents which significantly inhibits tumor cell growth with low toxicity. Tumor growth and development in mammals is reduced following administration of a combination of a topoisomerase I inhibitor and an inhibitor of angiogenesis. Accordingly, the invention provides an antineoplastic formulation containing a camptothecin compound and a thrombospondin compound. The camptothecin compound is camptothecin or an analogue thereof, e.g., irinotecan (camptosar, CPT-11, 7-ethyl-10-[4-(1-piperidino)-1-piperidino]-carbonloxycamptothecin), topotecan, 20-S-camptothecin (20(S)CPT), 10,11-methylenedioxy-CPT (10, 11-CPT), 7-ethyl-10-hydroxy-CPT (SN38), 9-AC$^3$ (NSC603071), TTN (NSC 609699), or 9-dimethylaminomethyl-10-hydroxycamptothecin. A thrombospondin compound is a polypeptide which contains at least one type I properdin repeat sequence and inhibits formation of blood vessels. For example, the thrombospondin compound is purified or recombinant thrombospondin-1(TSP1) or thrombospondin-2 (TSP2) or a biologically active fragment thereof. Preferably, a biologically active fragment contains the amino acid sequence XXXWXXWXXWXXCXXXXXXXXXXXXXXCXXXX-XXXXXXXXXXXXXXXXXX CXXXXC (SEQ ID NO:1), WSPS (SEQ ID NO:2), KRFK (SEQ ID NO:3), or CSVTCG (SEQ ID NO:4). For example, a fragment of TSP1 contains the amino acid sequence DGGWSHWSPWSSCS-VTCGDGVITRIRLCNSPSPQMNGK-PCEGEARETKACKKDACP I (SEQ ID NO:5), and a fragment of TSP2 contains the amino acid sequence of DGGWSHWSPWSSCSVTCGVGNITRIRL-CNSPVPQMGGKNCKGSGRETKACQGAPCP I (SEQ ID NO:6).

Also within the invention is method of inhibiting tumor cell growth in a mammal by administering to the mammal a composition containing an inhibitor of angiogenesis and an inhibitor of DNA topoisomerase I enzyme activity. The angiogenesis inhibitor is administered before the topoisomerase inhibitor; alternatively the topoisomerase I inhibitor is administered before the angiogenesis inhibitor. In some cases, the inhibitors are administered simultaneously. For example, the method includes the steps of administering to the mammal a camptothecin compound and a thrombospondin compound. Preferably, the mammal is a human; however, the methods are applicable for veterinary use. For example, the agents are administered to treat tumors in cats, dogs, cows, pigs, and the like. The compounds are administered together in a mixture, simultaneously via the same or different route, or sequentially via the same or different route. The compositions are delivered systemically or locally, i.e., directly or in close proximity to a tumor mass.

The combination drug formulation and methods of the invention are safer and more effective than conventional chemotherapeutic approaches, including known combination approaches. The combination of a camptothecin compound and a thrombospondin compound inhibited tumor growth in the absence of significant toxicity.

Other features, objects, and advantages of the invention will be apparent from the description and and from the claims.

DETAILED DESCRIPTION

Angiogenesis inhibitors and inhibitors of topoisomerase I such as camptothecin compounds are used to treat tumors in mammals; however, each of these agents alone is not effective in the treatment of human cancers. The combined therapeutic regimen results in a synergistic inhibition of tumor cell growth. As is described below, a combination of these agents confers greater neoplastic activity than either of these classes of agents alone.

Inhibition of DNA Topoisomerase I Enzymes

DNA topoisomerase type 1 enzymes function to effect the levels of DNA supercoiling. A biological activity of topoisomerase I is reduction in the level of DNA supercoiling. DNA transformations performed by DNA topoisomerases are accomplished by the cleavage of either a single strand or both strands the nucleic acid. Type 1 topoisomerases can relax supercoiled DNA (except of reverse gyrases), catenate (or decatenate) single-stranded circular DNAs or duplexes providing that at least one of the molecules contains a nick or gap, or interact with single-stranded circles to introduce topological knots.

Enzyme inhibition leads to the stabilization of the covalent-enzyme-DNA complex (cleavable complex). Topoisomerase type I inhibitory activity of camptothecin or derivatives thereof is determined using methods known in the art, e.g., by the cleavable complex in vitro assay described in Hsiang, Y. et al., 1985, J. Biol. Chem., 260:14873–14878. An increase in the amount of compound in the presence of a compound compared to the amount in the absence of the compound indicates that the compound has topoisomerase I inhibitory activity. Activity measured by this or similar assays correlates well with in vivo antitumor activity of topoisomerase inhibitors in animal models of cancer, e.g., camptothecin and its analogs (Hsiang et al., 1989, Cancer Research, 49:4385–4389 (1989) and Jaxel et al., Cancer Research, 49:1465–1469).

Camptothecin Compounds

Camptothecin is a naturally-occurring compound derived from the Oriental tree *Camptotheca acuminata*. Although it has been shown to have cytotoxic effects, its use clinically is limited due to unpredictable and formidable toxicities. Two water-soluble camptothecin analogs, topotecan and CPT-11, are safer and better tolerated. Additional water soluble camptothecins are known in the art, e.g., described in U.S. Pat. No. 6,100,273. Other camptothecin derivatives include 20-S-camptothecin (20(S)CPT), 10,11-methylenedioxy-CPT (10,11-CPT) and 7-ethyl-10-hydroxy-CPT (SN38). Camptothecin and its derivatives are inhibitors of DNA topoisomerase and stimulate DNA cleavage. Other topoisomerase I inhibitors include DNA minor groove binders such as Hoechst 33258 and DNA intercalators such as benzophenanthridine alkaloids and indolocarbazole derivatives, as well as drugs which prevent or reverse topoisomerase I-DNA complex formation (e.g., beta-lapachone, diospyrin, topostatin, topostin, flavonoids).

Inhibition of Angiogenesis

Angiogenesis is a process of tissue vascularization that involves the growth of new developing blood vessels into a tissue. This process is also referred to as neovascularization and is mediated by infiltration of endothelial cells and smooth muscle cells. Blood vessels can sprout from pre-existing vessels, de-novo development of vessels can arise from precursor cells (vasculogenesis), or existing small vessels can enlarge in diameter.

Inhibiting angiogenesis at or near a tumor site can restrict tumor growth. Inhibitors of angiogenesis include endothelial cell response inhibitors, including collagenase inhibitors, basement membrane turnover inhibitors, angiostatic steroids, fungal-derived angiogenesis inhibitors, platelet factor 4, thrombospondin, arthritis drugs such as D-penicillamine and gold thiomalate, vitamin D analogs, and alpha-interferon.

Angiogenesis or inhibition thereof is determined by measuring the formation of "microvessels" in vitro in collagen gel cultures or in vivo. A reduction in the amount of new blood vessel formation in the presence of a compound compared to the level in the absence of the compound indicates that the compound is an inhibitor of angiogenesis. A reduction in the amount of expression of angiogenic factors, e.g., vascular endothelial growth factor (VEGF) or VEGF receptors also indicates that a compound inhibits angiogenesis.

Thrombospondin Compounds

Thrombospondins are polypeptide compounds which are characterized by a type I (properdin) repeat, e.g., SEQ ID NO:1, 5 or 6. Thrombospondin-1 is a 450 kDa extracellular matrix protein that functions to suppresses capillary growth. The antiangiogenic region of TSP1 maps to the type I (properdin) repeats. Naturally-occurring TSP1 is a trimeric extracellular matrix protein that is held together by two cysteine residues. It is one of a family of five TSP proteins that have been described to date. With the exception of TSP5, members of the thrombospondin family are also characterized as having heparin binding capability. However, a heparin binding domain (e.g., located in the amino terminal portion of a naturally-occurring thrombospondin monomer) need not be present for antiangiogenic activity.

Biologically active fragments, mutants, or analogues of TSP1 or TSP are tested for the ability to inhibit angiogenesis. Fragments are recombinantly produced or generated by enzymatic digestion. Fragments and analogues of human thrombospondin with antiangiogensis activity are known in the art (e.g., as described in U.S. Pat. No. 5,192,744 or U.S. Pat. No. 5,840,692). Inhibition of angiogenesis is measured using methods well known in the art, e.g., a standard in vivo corneal neovascularization assay (Polverini et al., 1991, Methods. Enzymol. 198:440–450).

Therapeutic Administration

Camptothecin or thrombospodin compounds are formulated as colloidal dispersions or dissolved in a pharmaceutically-acceptable diluent, e.g., sterile water, physiological saline, or a dextrose solution (e.g., 20% dextrose). Alternatively, a camptothecin compound is administered as a liposomal composition; methods for preparing multilamellar liposome-incorporated camptothecin (LCPT) are known in the art (e.g., as described by Clements et al., 1996, Anticancer Drugs 7:851).

The combination drug therapy is used to treat solid, non-solid, and multiple-drug resistant tumors. The tumor is a carcinoma or sarcoma. Tumors to be treated include leukemia, lymphoma, as well as cancers of the colon, lung, melanoma, ovarian, breast, prostate cancer, pancreatic, CNS, liver, and urinary bladder.

An effective amount of a compound is preferably from about 0.1 mg/kg to about 150 mg/kg. The compounds are administered using methods known in the art. They are administered locally, e.g., at the site of a solid tumor, or systemically, e.g., in the case of diffuse, or disseminated tumors. To treat accessible solid tumors, either agent or both agents are administered in a slow release implant or pellets surgically introduced into or near the site of a solid tumor. Preferably, the compound is administered orally, topically or parenterally, e.g., subcutaneously, intraperitoneally, intramuscularly, and intravenously. The compounds are administered as an admixture, or in separate formulations either simultaneously, or sequentially.

Thrombospondin-1 and Irinotecan Inhibit Tumor Growth

The antineoplastic activity of TSP plus CPT-11 was evaluated in an art-recognized model for cancer, nude mice bearing xenografts of the human colon tumor cell line HT29. TSP and CPT-11 did not interact in vitro to produce enhanced tumor cell cytotoxicity. However, in vivo, a synergistic antineoplastic effect was observed after administration of TSP and CPT-11 in combination.

For in vivo studies, nude mice were inoculated subcutaneously in the left axillary region with $5 \times 10^6$ HT29 cells. When tumors were palpable (approximately 50 mg), mice were divided into groups (n=15–22) and treated as follows: (i) no treatment; (ii) TSP alone (5–40 mg/kg intraperitoneally) (iii) CPT-11 alone (100–300 mg/kg intraperitoneally); or (iv) TSP (20 mg/kg)+CPT-11 (150 mg/kg). TSP was injected daily while CPT-11 was administered on days 0, 7, 14, and 21. Mice were weighed and tumors measured twice weekly. By day 28, TSP alone (10 or 20 mg/kg) significantly ($p<0.05$) inhibited tumor growth. Treated tumor size/Control tumor size (T/C) equaled 0.64 or 0.57, respectively. Treatment with other doses of TSP was less effective. CPT-11 alone, at all doses, also significantly ($p<0.001$) inhibited tumor growth with and average T/C of 0.3. However, CPT-11 at 250 mg/kg and 300 mg/kg induced significant toxicity and mortality. When TSP was combined with CPT-11, a highly significant inhibition of tumor growth was observed compared to control (T/C=0.1, with p=0.00002) and compared to CPT-11 alone (p=0.0008).

The inhibition of tumor growth observed with the combination drug therapy was without significant toxicity. These results indicate that combinations of chemotherapeutic agents (e.g., topoisomerase I inhibitors such as camptothecins) and agents which inhibit angiogenesis (e.g., thrombospondins) are useful to inhibit tumor growth while avoiding detrimental side effects such as toxicity.

Other embodiments are within the following claims.

---

What is claimed is:

1. A method of inhibiting tumor cell growth in a mammal, comprising administering to said mammal a composition comprising a thrombospondin polypeptide and an inhibitor of DNA topoisomerase I enzyme activity, wherein said tumor cell is a colon tumor cell, wherein said thrombospondin polypeptide is thrombospondin-1 (TSP-1) or thrombospondin-2 (TSP-2) and said inhibitor of DNA topoisomerase I enzyme activity is irinotecan (CPT-11) and wherein administering the composition produces a synergistic antineoplastic effect in said mammal such that tumor growth is inhibited in the presence of said thrombospondin polypeptide and said water soluble camptothecin compound compared to in the absence of said thrombospondin polypeptide and said water soluble camptothecin compound.

2. The method of claim 1, wherein said thrombospondin polypeptide is thrombospondin-1.

3. The method of claim 1, wherein said thrombospondin polypeptide is thrombospondin-2.

4. The method of claim 1, wherein said mammal is a human.

5. The method of claim 1, wherein said thrombospondin polypeptide is administered prior to said inhibitor of DNA topoisomerase I enzyme activity.

6. The method of claim 1, wherein said inhibitor of DNA topoisomerase I enzyme activity is administered prior to said thrombospondin polypeptide.

7. The method of claim 1, wherein said thrombospondin polypeptide and said inhibitor of DNA topoisomerase I enzyme activity are administered simultaneously.

* * * * *